United States Patent
Levanon

(10) Patent No.: US 10,204,642 B2
(45) Date of Patent: Feb. 12, 2019

(54) EMOTIONAL SURVEY ACCORDING TO VOICE CATEGORIZATION

(71) Applicant: BEYOND VERBAL COMMUNICATION LTD, Tel-Aviv (IL)

(72) Inventor: Yoram Levanon, Ramat Hasharon (IL)

(73) Assignee: BEYOND VERBAL COMMUNICATION LTD, Tel-Aviv (IL)

( * ) Notice: Subject to any disclaimer, the term of this patent is extended or adjusted under 35 U.S.C. 154(b) by 0 days.

(21) Appl. No.: 14/910,046

(22) PCT Filed: Aug. 3, 2014

(86) PCT No.: PCT/IL2014/050699
§ 371 (c)(1),
(2) Date: Feb. 4, 2016

(87) PCT Pub. No.: WO2015/019345
PCT Pub. Date: Feb. 12, 2015

(65) Prior Publication Data
US 2016/0196837 A1  Jul. 7, 2016

Related U.S. Application Data

(60) Provisional application No. 61/862,553, filed on Aug. 6, 2013.

(51) Int. Cl.
*G10L 17/26* (2013.01)
*G10L 25/63* (2013.01)
(Continued)

(52) U.S. Cl.
CPC .............. *G10L 25/63* (2013.01); *A61B 5/165* (2013.01); *A61B 5/4803* (2013.01);
(Continued)

(58) Field of Classification Search
CPC ................................. G10L 25/63; G10L 17/26
See application file for complete search history.

(56) References Cited

U.S. PATENT DOCUMENTS 6,151,571 A * 11/2000 Pertrushin ............... G10L 17/26
  704/207
6,638,217 B1   10/2003 Liberman
(Continued)

FOREIGN PATENT DOCUMENTS

WO      2015/019345 A1    2/2015

OTHER PUBLICATIONS

International Search Report of PCT/IL2014/050699, dated Nov. 15, 2014.
Written Opinion of PCT/IL2014/050699, dated Nov. 15, 2014.

*Primary Examiner* — Michael N Opsasnick

(57) ABSTRACT

A method for determining emotional status of a group of N people comprising steps of: receiving an audio data of at least one person from the group of N people by a computer readable medium (CRM); determining emotional status of that person according to the received audio data using the CRM; repeating the steps of receiving and determining for a sub-group of M people selected from the group N people; M is an integer between 1 and N; the method additionally comprising step of determining emotional status of the group by applying a statistical function on plurality of the emotional status collected in the steps mentioned above.

21 Claims, 2 Drawing Sheets

(51) Int. Cl.
*A61B 5/16* (2006.01)
*A61B 5/00* (2006.01)
*G06F 19/00* (2018.01)

(52) U.S. Cl.
CPC ............ *A61B 5/7275* (2013.01); *G06F 19/00* (2013.01); *G10L 17/26* (2013.01)

(56) References Cited

U.S. PATENT DOCUMENTS

| | | | |
|---|---|---|---|
| 7,917,366 B1* | 3/2011 | Levanon | G10L 17/26 434/236 |
| 8,078,470 B2 | 12/2011 | Levanon et al. | |
| 9,202,251 B2* | 12/2015 | Bist | G06F 17/30032 |
| 2008/0091515 A1* | 4/2008 | Thieberger | G06Q 10/063 705/7.11 |
| 2008/0270123 A1* | 10/2008 | Levanon | G10L 17/26 704/200.1 |
| 2008/0270138 A1 | 10/2008 | Knight et al. | |
| 2009/0313019 A1* | 12/2009 | Kato | G10L 17/26 704/254 |
| 2011/0142413 A1* | 6/2011 | Kang | A61B 5/165 386/234 |
| 2011/0178803 A1* | 7/2011 | Petrushin | G10L 17/26 704/270 |
| 2012/0316883 A1 | 12/2012 | Levanon et al. | |
| 2013/0211845 A1* | 8/2013 | Imparato | G10L 25/63 704/278 |
| 2014/0366049 A1* | 12/2014 | Lehtiniemi | H04N 21/44218 725/12 |
| 2016/0249842 A1* | 9/2016 | Ohana Lubelchick | A61B 5/165 704/237 |

\* cited by examiner

EMOTIONAL SURVEY ACCORDING TO VOICE CATEGORIZATION

RELATED APPLICATIONS

This application is a U.S. National Phase Application which claimes benefit under 35 U.S.C. 371 from PCT Application No. PCT/IL2014/050699, filed on Aug. 3, 2014, and claims priority from U.S. Provisional Application No. 61/862,553, filed on Aug. 3, 2013.

U.S. Pat. No. 7,917,366, entitled "SYSTEM AND METHOD FOR DETERMINING A PERSONAL SHG PROFILE BY VOICE ANALYSIS" filed Sep. 28, 2006, is hereby incorporated by reference in its entirety.

U.S. Pat. No. 8,078,470, entitled "SYSTEM FOR INDICATING EMOTIONAL ATTITUDES THROUGH INTONATION ANALYSIS AND METHODS THEREOF" filed Dec. 20, 2006, is hereby incorporated by reference in its entirety.

FIELD OF THE INVENTION

The invention relates to the field of analyzing voice pattern, more specifically, it relates to the field of detecting emotional state according to the analysis.

BACKGROUND

Voice analysis is a rapidly growing field, especially due the latest technological progress. Computer power for analysis of data is constantly rising, and in addition, any mobile device these days may act as a recording mean for audio data. Many calls application now go through electronic devices enabling them to store the voice data for future analysis.

U.S. Pat. No. 7,917,366 (refers hereinafter as 366') discloses means and method for determining an emotional state of an individual using voice analysis. However, 366' fails to disclose voice analysis of a group of people and receiving an indication of emotional trends in the world.

There is therefore a long unmet need for means and method for understanding emotional trends of a large group of people.

SUMMARY OF THE INVENTION

It is one object of the current invention to disclose a method for determining emotional status of a group of N people comprising steps of:
  a. receiving an audio data of at least one person from the group by a computer readable medium (CRM);
  b. determining emotional status of at least one person according to the audio data using the CRM;
  c. repeating steps (a)-(b) for a sub-group of M people selected from the group; M is an integer between 1 and N;
  wherein the method additionally comprising step of:
  d. determining emotional status of the group by applying a statistical function on plurality of emotional status collected in steps (a)-(c).

It is an object of the current invention to disclose the method as described above, additionally comprising step of producing at least one of: (i) function of normalized intensity as function of frequency from each of the audio data; (ii) function of maximum intensity as function of frequency from each of the audio data.

It is an object of the current invention to disclose the method as described above, wherein step (b) is performed by grading the function according to either one of TABLES 1-8.

It is an object of the current invention to disclose the method as described above, wherein the high energy refers to an energy mark higher or equal to 650 HZ.

It is an object of the current invention to disclose the method as described above, wherein the high energy refers to an energy mark higher or equal to 850 HZ.

It is an object of the current invention to disclose the method as described above, wherein step (b) is performed by a matching algorithm between tones of the audio data and tones of an optimal model.

It is an object of the current invention to disclose the method as described above, wherein the audio data is received from a source selected from a group consisting of: phone conversation, microphone, call application on a mobile device, microphone installed in a public location and a combination thereof.

It is an object of the current invention to disclose the method as described above, additionally comprising step of storing historical data in a database.

It is an object of the current invention to disclose the method as described above, additionally comprising step of predicting future emotional state of the group by analyzing history of past emotional state.

It is an object of the current invention to disclose the method as described above, wherein step (b) is performed by method for indicating emotional status of a speaker according to voice tone, the method comprising:
  a. obtaining a database comprising reference tones and reference emotional status corresponding to each of the reference tones;
  b. pronouncing at least one word by a speaker for the duration of a sample period;
  c. recording at least one word so as to obtain a signal representing sound volume as a function of frequency for the sample period;
  d. processing the signal so as to obtain voice characteristics of the speaker, wherein the processing includes determining a Function A, the Function A being defined as the average or maximum sound volume as a function of sound frequency, from within a range of frequencies measured in the sampled period, and wherein the processing further includes determining a Function B, the Function B defined as the averaging, or maximizing of the function A over the range of frequencies and dyadic multiples thereof;
  e. comparing the voice characteristics to the reference tones so as to indicate at least one of the reference emotional status.

It is an object of the current invention to disclose the method as described above, wherein the statistical function is selected from a group comprising of average of the function arguments; average of the function arguments, including numbers, text, and logical values; beta cumulative distribution function; the inverse of the cumulative distribution function for a specified beta distribution; individual term binomial distribution probability; one-tailed probability of the chi-squared distribution; inverse of the one-tailed probability of the chi-squared distribution; test for independence; confidence interval for a population mean; covariance, the average of the products of paired deviations; smallest value for which the cumulative binomial distribution is less than or equal to a criterion value; sum of squares of deviations; exponential distribution; probability distribution; inverse of the F probability distribution; Fisher transformation; inverse of the Fisher transformation; value along a linear trend; frequency distribution as a vertical array; result of an F-test; gamma distribution; inverse of the gamma cumulative distribution; natural logarithm of the gamma function, $\Gamma(x)$; geometric mean; values along an exponential trend; harmonic mean; hypergeometric distribution; intercept of the linear regression line; kurtosis of a data set; k-th largest value in a data set; parameters of a linear trend; parameters of an exponential trend; inverse of the lognormal distribution; cumulative lognormal distribution; maximum value in a list of arguments; maximum value in a list of arguments, including numbers, text, and logical values; median of the given numbers; minimum value in a list of arguments; smallest value in a list of arguments, including numbers, text, and logical values; most common value in a data set; negative binomial distribution; normal cumulative distribution; inverse of the normal cumulative distribution; standard normal cumulative distribution; inverse of the standard normal cumulative distribution; Pearson product moment correlation coefficient; k-th percentile of values in a range; percentage rank of a value in a data set; number of permutations for a given number of objects; Poisson distribution; probability that values in a range are between two lim; quartile of a data set; rank of a number in a list of numbers; square of the Pearson product moment correlation coefficient; skewness of a distribution; slope of the linear regression line; k-th smallest value in a data set.

It is another object of the current invention to disclose a system for determining emotional status of a group of N people comprising:

a plurality of M audio data of M people from the group stored on a computer readable medium (CRM) having instruction thereon for determining emotional status of each of M people according to the audio data; M is an integer smaller than N;

wherein the instruction are further for determining emotional status of the group by applying a statistical function on plurality of the emotional status determined for the M people.

It is an object of the current invention to disclose the system as described above, wherein the instructions are additionally for producing at least one of: (i) function of normalized intensity as function of frequency from each of the audio data; (ii) function of maximum intensity as function of frequency from each of the audio data.

It is an object of the current invention to disclose the system as described above, wherein the determining emotional status is performed by grading the function according to either one of TABLES 1-8.

It is an object of the current invention to disclose the system as described above, wherein the high energy refers to an energy mark higher or equal to 650 HZ.

It is an object of the current invention to disclose the system as described above, wherein the high energy refers to an energy mark higher or equal to 850 HZ.

It is an object of the current invention to disclose the system as described above, wherein the determining emotional status is performed by a matching algorithm between (i) tones of the audio data and (ii) tones of an optimal model.

It is an object of the current invention to disclose the system as described above, wherein the audio data is received from a source selected from a group consisting of: phone conversation, microphone, call application on a mobile device, microphone installed in a public location and a combination thereof.

It is an object of the current invention to disclose the system as described above, additionally comprising storage means for storing historical data.

It is an object of the current invention to disclose the system as described above, wherein the instructions are additionally for predicting future emotional state of the group by analyzing history of past emotional state.

It is an object of the current invention to disclose the system as described above, wherein the statistical function is selected from a group comprising of average of the function arguments; average of the function arguments, including numbers, text, and logical values; beta cumulative distribution function; the inverse of the cumulative distribution function for a specified beta distribution; individual term binomial distribution probability; one-tailed probability of the chi-squared distribution; inverse of the one-tailed probability of the chi-squared distribution; test for independence; confidence interval for a population mean; covariance, the average of the products of paired deviations; smallest value for which the cumulative binomial distribution is less than or equal to a criterion value; sum of squares of deviations; exponential distribution; probability distribution; inverse of the F probability distribution; Fisher transformation; inverse of the Fisher transformation; value along a linear trend; frequency distribution as a vertical array; result of an F-test; gamma distribution; inverse of the gamma cumulative distribution; natural logarithm of the gamma function, $\Gamma(x)$; geometric mean; values along an exponential trend; harmonic mean; hypergeometric distribution; intercept of the linear regression line; kurtosis of a data set; k-th largest value in a data set; parameters of a linear trend; parameters of an exponential trend; inverse of the lognormal distribution; cumulative lognormal distribution; maximum value in a list of arguments; maximum value in a list of arguments, including numbers, text, and logical values; median of the given numbers; minimum value in a list of arguments; smallest value in a list of arguments, including numbers, text, and logical values; most common value in a data set; negative binomial distribution; normal cumulative distribution; inverse of the normal cumulative distribution; standard normal cumulative distribution; inverse of the standard normal cumulative distribution; Pearson product moment correlation coefficient; k-th percentile of values in a range; percentage rank of a value in a data set; number of permutations for a given number of objects; Poisson distribution; probability that values in a range are between two lim; quartile of a data set; rank of a number in a list of numbers; square of the Pearson product moment correlation coefficient; skewness of a distribution; slope of the linear regression line; k-th smallest value in a data set.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. In the accompanying drawing:

DETAILED DESCRIPTION OF THE INVENTION

Figure 1:
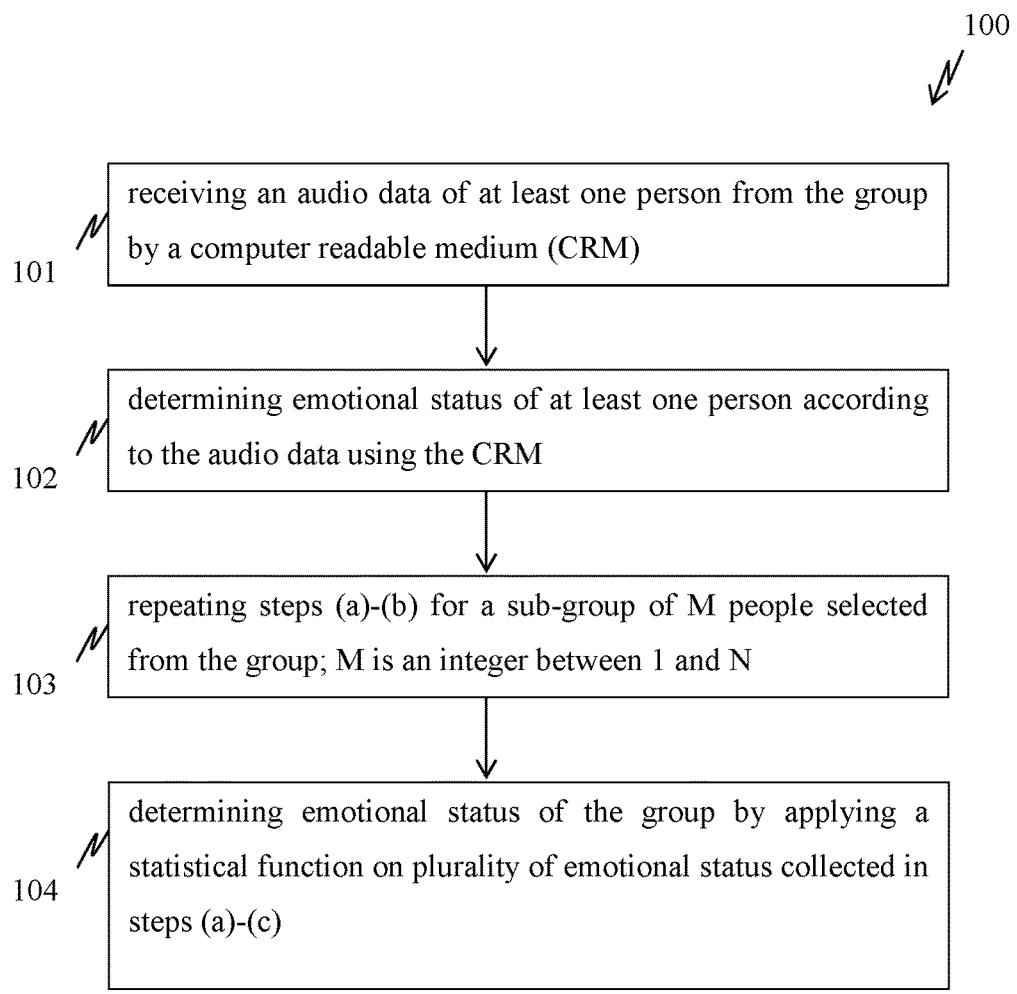
FIG. 1 is a schematic flow diagram for a method for determining emotional status of a group of N people.
Figure 2:
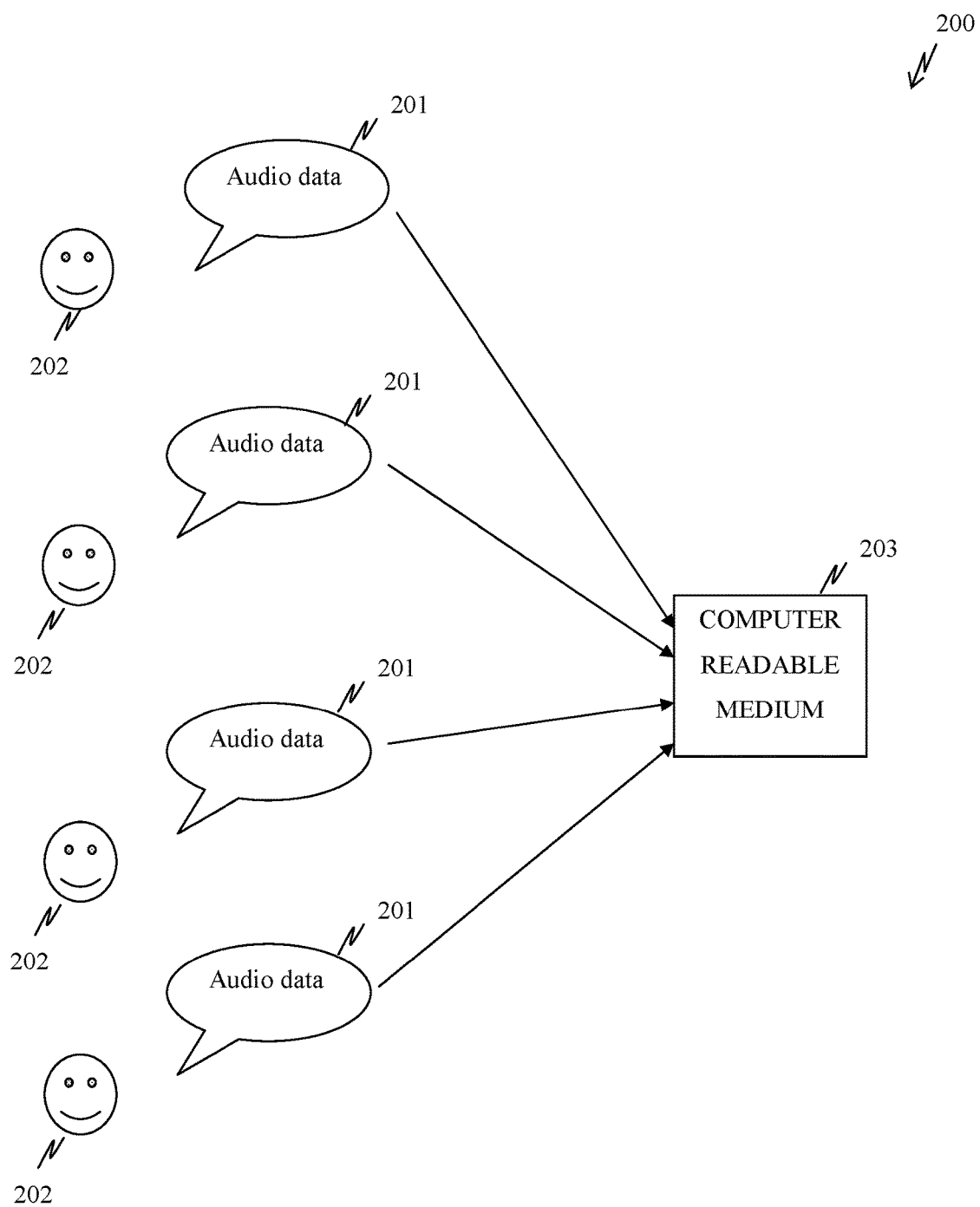
FIG. 2 is a block diagram of a system for determining emotional status of a group of N people

The following description is provided, alongside all chapters of the present invention, so as to enable any person skilled in the art to make use of the invention and set forth the best modes contemplated by the inventor of carrying out this invention. Various modifications, however, will remain apparent to those skilled in the art.

It is one object of the current invention to disclose a method for determining emotional status of a group of N people comprising steps of:
  a. receiving an audio data of at least one person from the group by a computer readable medium (CRM);
  b. determining emotional status of at least one person according to the audio data using the CRM;
  c. repeating steps (a)-(b) for a sub-group of M people selected from the group; M is an integer between 1 and N;
  wherein the method additionally comprising step of:
  d. determining emotional status of the group by applying a statistical function on plurality of emotional status collected in steps (a)-(c).

It is another object of the current invention to disclose a system for determining emotional status of a group of N people comprising:
  a plurality of M audio data of M people from the group stored on a computer readable medium (CRM) having instruction thereon for determining emotional status of each of the M people according to the audio data; M is an integer smaller than N;
  wherein the instruction are further for determining emotional status of the group by applying a statistical function on plurality of the emotional status determined for a the M people.

The term "emotional state", refers hereinafter to any emotion of: affection, anger, angst, anguish, annoyance, anxiety, apathy, arousal, awe, boldness, boredom, contempt, contentment, curiosity, depression, desire, despair, disappointment, disgust, distrust, dread, ecstasy, embarrassment, envy, euphoria, excitement, fear, fearlessness, frustration, gratitude, grief, guilt, happiness, hatred, hope, horror, hostility, hurt, hysteria, indifference, interest, jealousy, joy, loathing, loneliness, love, lust, misery, panic, passion, pity, pleasure, pride, rage, regret, remorse, sadness, satisfaction, shame, shock, shyness, sorrow, suffering, surprise, terror, trust, wonder, worry, zeal, zest, lack of interest, self-control, interpersonal communication, pragmatism, survival, conservatism, creativeness, inspiration, leadership, authority, preaching, admiring, envying, aggressiveness, hypocrisy, possessiveness, and any combination thereof.

The term "energy mark" refers hereinafter to the frequency in which the normalized intensity is of 20%.

The term "octave" refers herein after to the interval between one musical pitch and another with half or double its frequency.

The term "average intensity function", refers herein after to a function calculated across the plurality of frequencies by averaging, at each of the plurality of frequencies, a plurality of sample intensity values of the speech. In one example the average intensity function may be computed by measuring the intensity of the speaker's voice during the time period "T" (in one example, T may be a relatively short span of a few dozen seconds). The average voice intensity is measured by measuring the intensities of sound at each different frequency, in the frequency range of between, for example, 20 Hz and 15000 Hz, during multiple time-points within the range T. The time-points (T1) may be selected to be equally distributed during the total range T. At each time-point, the intensity of each frequency is measured and is described as a function "F1" of that frequency I (F1, T1). This measurement is repeated at every time-point for a total of "N" measurements to span the entire range T. Thus, in this example, the average intensity function for each frequency can be described as:

$$I(f0) = 1/n \Sigma ni = I(f0, T1)$$

The term "maximum intensity function", refers herein after to a function calculated across the plurality of frequencies by determining, at each of the plurality of frequencies, a maximum of a plurality of sample intensity values of the speech. In one example essentially the same voice intensity measurements that were described for the average intensity function may be collected. In this example, the maximum intensity function will be arrived at (during the time T) by the equation: $mIMAX(f0) = MAX[I(f0, T)]$ Reference is now made to FIG. 1 illustrating in a non-limiting manner a flow chart for a method 100 for determining emotional status of a group of N people comprising:
  a. step 101 of receiving an audio data of at least one person from the group by a computer readable medium (CRM);
  b. step 102 of determining emotional status of at least one person according to the audio data using the CRM;
  c. step 103 of repeating steps (a)-(b) for a sub-group of M people selected from the group; M is an integer between 1 and N;
  wherein the method additionally comprising step of:
  d. step 104 of determining emotional status of the group by applying a statistical function on plurality of emotional status collected in steps (a)-(c).

Reference is now made to FIG. 1 illustrating in a non-limiting manner a block diagram 200 for a system for determining emotional status of a group of N people comprising:
  a plurality of M audio data 201 of M people 202 from the group stored on a computer readable medium (CRM) 203 having instruction thereon for determining emotional status of each of the M people 202 according to the audio data 201; M is an integer smaller than N;
  wherein the instruction are further for determining emotional status of the group by applying a statistical function on plurality of the emotional status determined for the M people.

In some embodiments of the current invention, the data may be recorded on a tape, a CD or any type of digital media like a computer, smart-phone or a tablet. A professional recording in a studio with no interruptions background noise is preferable but also a simple home recording in a quite environment will be sufficient for the analysis.

In some embodiments of the current invention the instruction of the CRM as described above instructions are additionally for producing at least one of: (i) function of normalized intensity as function of frequency from each of the audio data; (ii) function of maximum intensity as function of frequency from each of the audio data.

In some embodiments of the current invention as described above, the determination of the emotional status is performed by grading either of the functions according to either one of TABLES 1-8 as described below.

In some embodiments of the current invention as described above, high energy may refer to an energy mark higher or equal to 650 HZ, or in other embodiments higher or equal to 850 HZ In some embodiments of the current invention as described above, determining emotional status is performed by a matching algorithm between (i) tones of the audio data and (ii) tones of an optimal model. One example of such matching algorithm is described below.

In some embodiments of the current invention as described above, the audio data is received from a source selected from a group consisting of: phone conversation, microphone, call application on a mobile device, microphone installed in a public location and a combination thereof.

In some embodiments of the current invention as described above, there is additional storage means for storing historical data.

In some embodiments of the current invention as described above, the instructions on the CRM are additionally for predicting future emotional state of the group by analyzing history of past emotional state.

In some embodiments of the current invention as described above, the statistical function is selected from a group comprising of average of the function arguments; average of the function arguments, including numbers, text, and logical values; beta cumulative distribution function; the inverse of the cumulative distribution function for a specified beta distribution; individual term binomial distribution probability; one-tailed probability of the chi-squared distribution; inverse of the one-tailed probability of the chi-squared distribution; test for independence; confidence interval for a population mean; covariance, the average of the products of paired deviations; smallest value for which the cumulative binomial distribution is less than or equal to a criterion value; sum of squares of deviations; exponential distribution; probability distribution; inverse of the F probability distribution; Fisher transformation; inverse of the Fisher transformation; value along a linear trend; frequency distribution as a vertical array; result of an F-test; gamma distribution; inverse of the gamma cumulative distribution; natural logarithm of the gamma function, $\Gamma(x)$; geometric mean; values along an exponential trend; harmonic mean; hypergeometric distribution; intercept of the linear regression line; kurtosis of a data set; k-th largest value in a data set; parameters of a linear trend; parameters of an exponential trend; inverse of the lognormal distribution; cumulative lognormal distribution; maximum value in a list of arguments; maximum value in a list of arguments, including numbers, text, and logical values; median of the given numbers; minimum value in a list of arguments; smallest value in a list of arguments, including numbers, text, and logical values; most common value in a data set; negative binomial distribution; normal cumulative distribution; inverse of the normal cumulative distribution; standard normal cumulative distribution; inverse of the standard normal cumulative distribution; Pearson product moment correlation coefficient; k-th percentile of values in a range; percentage rank of a value in a data set; number of permutations for a given number of objects; Poisson distribution; probability that values in a range are between two lim; quartile of a data set; rank of a number in a list of numbers; square of the Pearson product moment correlation coefficient; skewness of a distribution; slope of the linear regression line; k-th smallest value in a data set.

Analysis of Voice Data

The analysis of the voice data, and the analysis of the voice data is performed by the method described in U.S. Pat. No. 8,078,470, incorporated here by reference.

Outbreak Prediction

The analysis of the single voice data, may be performed, in some embodiments of the current invention, by grading the analyzed tones of the data. Four tones are selected from the audio data according to some predetermined parameters. And according to these four tones different grading is given to the original data according to the following table:

TABLE 1

| Four tones comprising: | grade |
|---|---|
| At least two tones of: DO DO# RE RE#; and one or two of: SI FA FA# SOL# LA | 20 |
| At least two tones of: SI FA FA# SOL# LA; and one or more of: DO DO# RE RE# | 20 |
| One tone of: DO DO# RE RE#; and one or more of: SI FA FA# SOL# LA | 15 |
| Two tones of: DO DO# RE RE#; and none of: SI FA FA# SOL# LA | 10 |
| Two tones of: SI FA FA# SOL# LA; and none of: DO DO# RE RE# | 10 |
| One tone of: DO DO# RE RE#; and none of: SI FA FA# SOL# LA | 5 |
| One tone of: SI FA FA# SOL# LA; and none of: DO DO# RE RE# | 5 |

In some embodiments of the current invention, the four tones as mentioned in Table 1, are selected from the tones in the voice data recorded and presented as function of normalized intensity as function of frequency. They are selected in the following manner: the tone with the highest intensity, the tone with the second highest intensity, the tone with the largest number of peaks, and the tone with the second largest number of peaks.

A different grading method may be, in some embodiments of the current invention, by determining the S-level of the audio data. The S-level of Table 2, is measured according to the method described in U.S. Pat. No. 7,917,366 incorporated here as reference. For each S-level, grading is given to the original audio data, according to the following Table:

TABLE 2

| S - level | grade |
|---|---|
| Change in 4 points | 5 |
| $S \geq 20$ | 20 |
| $19 \geq S \geq 17$ | 15 |
| $16 \geq S \geq 15$ | 10 |
| $14 \geq S \geq 13$ | 5 |

In some other embodiments of the current invention, grading is given according to the following profile and characterization of the audio data:

TABLE 3

| Value of the tones- [DO, DO#, RE, RE#, FA, FA#, SOL, SOL#, LA, LA#, SI] in the normalized maximum function of the OCTAVE 4185 Hz-2092 Hz. Valid for energy mark ≥850 HZ | grade |
|---|---|
| All higher than 60% | 20 |
| All higher than 40% | 15 |

TABLE 3-continued

Value of the tones- [DO, DO#, RE, RE#, FA, FA#,
SOL, SOL#, LA, LA#, SI] in the normalized maximum
function of the OCTAVE 4185 Hz-2092 Hz.

| Valid for energy mark ≥850 HZ | grade |
|---|---|
| All higher than 25% | 10 |
| All higher than 15% | 5 |

Another option for grading, in some other embodiments of the current invention, is given according to the following profile and characterization of the audio data:

TABLE 4

Value of the tones- [DO, DO#, RE, RE#, FA, FA#,
SOL, SOL#, LA, LA#, SI] in the normalized maximum
function of the OCTAVE 4185 Hz-2092 Hz.

| Valid for energy mark ≤850 HZ | grade |
|---|---|
| All higher than 60% | 10 |
| All higher than 40% | 7.5 |
| All higher than 25% | 5 |
| All higher than 15% | 2.5 |

There is yet another option for characterizing and grading audio data, according to ration of intensities as described in the following table which relates to the average intensity function:

TABLE 5

| Ratio between (i) intensity of each frequency in the octave (261 Hz-522 Hz); and (ii) intensity of same frequency in each of the octaves (532 Hz-1045 Hz), (1046 Hz-2092 Hz), (2092 Hz-4185 Hz). The intensity is as measured in the average intensity function. | grade |
|---|---|
| 1 ≤ ratio ≤ 1.2 | 5 |
| 1.21 ≤ ratio ≤ 1.5 | 10 |
| 1.51 ≤ ratio ≤ 3 | 15 |
| 3 ≤ ratio | 20 |

There is yet another option for characterizing and grading audio data, according to ration of intensities as described in the following table which relates to the maximum intensity function:

TABLE 6

| Ratio between (i) intensity of each frequency in the octave (261 Hz-522 Hz); and (ii) intensity of same frequency in each of the octaves (532 Hz-1045 Hz), (1046 Hz-2092 Hz), (2092 Hz-4185 Hz). The intensity is as measured in the maximum intensity function. | grade |
|---|---|
| 1 ≤ ratio ≤ 1.2 | 5 |
| 1.21 ≤ ratio ≤ 1.5 | 10 |
| 1.51 ≤ ratio ≤ 3 | 15 |
| 3 ≤ ratio | 20 |

A different grading method may be, in some embodiments of the current invention, by determining the S-level of the audio data. The H-level of Table 7, is measured according to the method described in U.S. Pat. No. 7,917,366 incorporated here as reference. For each H-level, grading is given to the original audio data, according to the following Table:

TABLE 7

| H - level | grade |
|---|---|
| Change in 5 points | 5 |

And in some embodiments of the current invention, grading is performed by all the methods described in TABLES 1-7, and all grading are summed-up. After receiving the final grading, the emotional status may be determined according to the following:

TABLE 8

| Sum of grades calculated in Tables 1-7 | Emotional status |
|---|---|
| 20 ≤ sum ≤ 30 | caution |
| 31 ≤ sum ≤ 45 | mild outbreak |
| 45 ≤ sum ≤ 60 | outbreak |
| 60 ≤ sum ≤ 80 | significant outbreak |
| 80 ≤ sum | severe outbreak |

Matching Algorithm

In some embodiments of the current invention, the matching algorithm is according to Table 9, Four tones are selected for either maximum intensity function or for average intensity function as follows: the tone with the highest intensity, the tone with the second highest intensity, the tone with the largest number of peaks, and the tone with the second largest number of peaks.

In TABLE 9, T1 marks the tone with the highest intensity as measured from the audio data, and Q1 is the tone with the highest intensity according to the optimal model. Each match receives a grade as described in TABLE. 9.

In some embodiments, for the four tones described above, there is a grading table with the optimal model. The marking of the tones as measured for the real data (either for the average function or the maximum function) are as follows:

T1—the tone with the highest intensity;
T2—the tone with the largest number of peaks;
T3—the tone with the second highest intensity; and
T4—the tone with the second largest number of peaks.

The marking of the tones as defined for the optimal model data are as follows:

Q1—the tone with the highest intensity;
Q2—the tone with the largest number of peaks;
Q3—the tone with the second highest intensity; and
Q4—the tone with the second largest number of peaks.

Determining the matching grade for a model Q1-Q4, is according to the following steps and using the tables for all combinations of T1-T4 and Q1-Q4:

For Q1—searching for the best fit (highest number) according to tables of Q1/T1-T4, the best fit number will be marked F1;

For Q2—searching for the best fit (highest number) according to tables of Q1/T1-T4 except the Ti which was matched with Q1, the best fit number will be marked F2.

For Q3—searching for the best fit (highest number) according to tables of Q1/T1-T4 except the Ti and Tj which was matched with Q1 and Q2 respectively, the best fit number will be marked F3.

For Q3—searching for the best fit (highest number) according to tables of Q1/T? which is the last T that was not matched, the best fit number will be marked F4.

Finally, the matching grade of the voice data will receive the grade of:
0.4F1+0.3F2+0.2F1+0.1F4.

In some embodiment of the current invention, a multiplication factor may be added to the entire grading TABLE according to specific emotional state that is being detected.

TABLE 9

| Q1 | T1 | | | | | | | | | | | |
|---|---|---|---|---|---|---|---|---|---|---|---|---|
|  | DO | DO# | RE | RE# | MI | FA | FA# | SOL | SOL# | LA | LA# | SI |
| DO | 1 | 0.9 | 0.8 | 0.7 | 0 | 0 | 0 | 0 | 0 | 0.5 | 0.7 | 0.8 |
| DO# | 0.9 | 1 | 0.9 | 0.8 | 0 | 0 | 0 | 0 | 0 | 0.3 | 0.5 | 0.7 |
| RE | 0.8 | 0.9 | 1 | 0.9 | 0.4 | 0.7 | 0.6 | 0.3 | 0.3 | 0.5 | 0.5 | 0.5 |
| RE# | 0.7 | 0.8 | 0.9 | 1 | 0.7 | 0.7 | 0.7 | 0.3 | 0.3 | 0.4 | 0.5 | 0.5 |
| MI | 0 | 0 | 0.4 | 0.7 | 1 | 0.7 | 0.5 | 0 | 0 | 0 | 0 | 0.3 |
| FA | 0 | 0 | 0.7 | 0.7 | 0.7 | 1 | 0.9 | 0.8 | 0.7 | 0.6 | 0.4 | 0 |
| FA# | 0 | 0 | 0.6 | 0.7 | 0.5 | 0.9 | 1 | 0.9 | 0.8 | 0.7 | 0.5 | 0 |
| SOL | 0 | 0 | 0.3 | 0.3 | 0 | 0.8 | 0.9 | 1 | 0.9 | 0.8 | 0.7 | 0.2 |
| SOL# | 0 | 0 | 0.3 | 0.3 | 0 | 0.7 | 0.8 | 0.9 | 1 | 0.9 | 0.8 | 0.4 |
| LA | 0.5 | 0.3 | 0.5 | 0.4 | 0 | 0.6 | 0.7 | 0.8 | 0.9 | 1 | 0.9 | 0.7 |
| LA# | 0.7 | 0.5 | 0.5 | 0.5 | 0 | 0.4 | 0.5 | 0.7 | 0.8 | 0.9 | 1 | 0.9 |
| SI | 0.8 | 0.7 | 0.5 | 0.5 | 0.3 | 0 | 0 | 0.2 | 0.4 | 0.7 | 0.9 | 1 |

At least one example of the current invention detects emotion state of a relationship. That is, a conversation is taking place between two individuals, and one of the individuals is recorded and analyzed. The analysis produces the four-tones as described above: T1, T2, T3, and T4. An optimal model for comparison is provided with four-tines: Q1, Q2, Q3, and Q4. And in addition, four tables are provided for grading the combinations of each of T1-4 with Q1-4 (an example for a table is provided in TABLE 9).

According to the best match between the optimal model tones and the recorded tones, the relationship status can be determined, as described in TABLE 10:

TABLE 10

| Application | Description | Q1 | Q2 | Q3 | Q4 |
|---|---|---|---|---|---|
| Relationship | Friendly showing interest talk | SOL | FA | RE | DO |
| Relationship | Cautious conversation | MI | SOL | DO | FA |
| Relationship | Warm conversation | SOL# | FA# | RE | LA# |
| Relationship | Confrontational talk | RE#* | SI* | DO* | SOL#* |
| Relationship | Desire talk | RE# | FA# | RE | LA |

*measured in high energy

Following the analysis of a single voice data, the same procedure may be performed on a plurality of people, each resulting in a different emotional state. For each of these emotional status, it is possible to perform a statistical data in order to determine the emotional status of the entire group, or on at least some sub-group.

The data collected during experiments may be stored in various methods. It may be stored and tagged according to each individual, a characterization of an individual or of a group or of a sub-group. The data collected may be analyzed and track historical activity of an individual, the entire group, sub-group, or any other tagging available. Following this analysis, it may be possible to predict any future emotional state of any of the above mentioned: individual, the entire group, sub-group, or any other tagging available. This time, the emotional state is determined according to prediction and not according to analysis of the current voice pattern.

An example for constructing this system may be as following: a company providing mobile application for free calls, records all the calls made during Christmas. The data is analyzed for each individual call, and receives a grade according to at least one of TABLE 1-7. The concluding emotional state of each individual is determined by TABLE 8. Following this analysis, an average on all emotional states collected is done, and the application presents on its GUI the emotional state of the country on Christmas.

It will be appreciated by persons skilled in the art that embodiment of the invention are not limited by what has been particularly shown and described hereinabove. Rather the scope of at least one embodiment of the invention is defined by the claims below.

The invention claimed is:

1. A method for apprising members of a second society about an emotional status pertaining to an emotional outbreak in a first society, said emotional status determined by sampling of M members of said first society speaking in telephone conversations, said method comprising steps of:
   a. for each of M members of a first society, simultaneously receiving, by a central computer, a voice recording of said member of the first society speaking into a microphone of a telephone in communicative connection with said central computer and storing said voice recording in a non-transitory computer readable medium (CRM) of said central computer;
   b. calculating, by a processor of said central computer, spectral functions of each said M voice recordings, comprising (i) a normalized intensity function and (ii) a maximum intensity function, and storing said spectral functions in said CRM;
   c. for each of said M voice recordings, calculating, by said processor, grades 1-7 according to said spectral functions and storing said grades 1-7 in said CRM;
   d. for each of said M voice recordings, adding said grades 1-7 and storing the grade sum in said CRM;
   e. calculating a group grade of said M members of the first society by applying a statistical function on said M grade sums and storing the group grade in said CRM;
   f. assigning an emotional status to said first society, according to said average grade sum; and
   e. displaying said emotional status on displays of computing devices of one or more members of a second society; said computing devices in communicative connection with said central computer;

wherein said step of calculating said grades 1-7 is performed for each of said voice recordings according to steps (h)-(n):

h. for calculating said grade 1,
  (i) selecting four tones in said normalized intensity function, comprising: 1) a tone with a highest intensity; 2) a tone with a second highest intensity; 3) a tone with a largest number of peaks; and 4) a tone with a second largest number of peaks; and
  (ii) assigning said grade 1 according to said four tones as follows:
    1. at least two tones of: DO DO# RE REM and one or two of: SI FA FA# SOL# LA corresponding to 20;
    2. at least two tones of: SI FA FA# SOL# LA; and one or more of: DO DO# RE RE# corresponding to 20;
    3. one tone of: DO DO# RE RE#; and one or more of: SI FA FA# SOL# LA corresponding to 15;
    4. two tones of: DO DO# RE RE#; and none of: SI FA FA# SOL# LA corresponding to 10;
    5. two tones of: SI FA FA# SOL# LA; and none of: DO DO# RE RE# corresponding to 10;
    6. one tone of: DO DO# RE RE#; and none of: SI FA FA# SOL# LA corresponding to 5; and
    7. one tone of: SI FA FA# SOL# LA; and none of: DO DO# RE RE# corresponding to 5;

i. for calculating at least one said grade 2,
  (i) determining an S-level in said voice recordings; and
  (ii) assigning at least one said grade 2 according to said S-level provides correspondence as follows:
    1. change by 4 corresponds to 5;
    2. S≥20 corresponds to 20;
    3. 19≥S≥17 corresponds to 15;
    4. 16≥S≥15 corresponds to 10; and
    5. 14≥S≥13 corresponds to 5;

j. for calculating said grade 3, applicable if energy mark ≥850 Hz,
  (i) determining values, for the tones DO, DO#, RE, RE#, FA, FA#, SOL, SOL#, LA, LA#, and SI, in the normalized maximum function of an octave 4185 Hz-2092 Hz; and
  (ii) assigning said grade 3 according to said values in the normalized maximum function as follows:
    1. all higher than 60% corresponds to 20;
    2. all higher than 40% corresponds to 15;
    3. all higher than 25% corresponds to 10; and
    4. all higher than 15% corresponds to 5;

k. for calculating said grade 4, applicable if said energy mark ≤850 Hz,
  (i) determining values, for the tones—[DO, DO#, RE, RE#, FA, FA#, SOL, SOL#, LA, LA#, SI] in the normalized maximum function of the OCTAVE 4185 Hz-2092 Hz;
  (ii) assigning said grade 4 according to said values in the normalized maximum function as:
    1. value of tones higher than 60% corresponds to 10;
    2. higher than 40% to 7.5;
    3. higher than 25% to 5; and
    4. higher than 15% to 2.5;

l. for calculating said grade 5,
  (i) determining a ratio in said average intensity function between 1) an intensity of each frequency in the octave (261 Hz-522 Hz); and (ii) intensity of same frequency in each of the octaves (532 Hz-1045 Hz), (1046 Hz-2092 Hz), (2092 Hz-4185 Hz); and
  (ii) assigning said grade 5 according to said ratio in said average intensity function as follows:
    1. If 1≤ratio≤1.2, to 5;
    2. If 1.21≤ratio≤1.5 10, to 10;
    3. If 1.51≤ratio≤3, to 15; and
    4. If 3≤ratio, to 20;

m. for calculating said grade 6,
  (i) determining a ratio in said maximum intensity function between 1) an intensity of each frequency in the octave (261 Hz-522 Hz); and (ii) intensity of same frequency in each of the octaves (532 Hz-1045 Hz), (1046 Hz-2092 Hz), (2092 Hz-4185 Hz); and
  (ii) assigning said grade 6 according to said ratio in said average intensity function [HM2] as follows:
    1. If 1≤ratio≤1.2, to 5;
    2. If 1.21≤ratio≤1.5 10, to 10;
    3. If 1.51≤ratio≤3, to 15; and
    4. If 3≤ratio, to 20; and n. for calculating said grade 7,
  (i) determining an H-level in said voice recording; and
  (ii) assigning a grade 7 of 5 if there is a change in 5 points in said H-level;

further wherein, o. said emotional status is assigned to said average grade sum as follows:
  1. average grade sum ranging between 20 and 30 corresponds to an emotional status of caution;
  2. between 31 and 45 to an emotional status of mild outbreak;
  3. between 45 and 60 to outbreak,
  4. between 60 and 80 to significant outbreak; and
  5. greater than 80 to severe outbreak.

2. The method according to claim 1, wherein said high energy refers to an energy mark higher or equal to 650 HZ.

3. The method according to claim 1, wherein said high energy refers to an energy mark higher or equal to 850 HZ.

4. The method according to claim 1, wherein said step (b) is further performed by a matching algorithm between tones of said audio data and tones of an optimal model.

5. The method according to claim 1, wherein said audio data is received from a source selected from a group consisting of: phone conversation, microphone, call application on a mobile device, microphone installed in a public location and a combination thereof.

6. The method according to claim 1, additionally comprising step of storing historical data in a database.

7. The method according to claim 1, additionally comprising step of predicting future emotional state of said group by analyzing history of past emotional state.

8. The method according to claim 1, wherein said step (b) is further performed by a method for indicating emotional status of a speaker according to voice tone, said method comprising:
  a. obtaining a database comprising reference tones and reference emotional status corresponding to each of said reference tones;
  b. pronouncing at least one word by a speaker for the duration of a sample period;
  c. recording said at least one word so as to obtain a signal representing sound volume as a function of frequency for said sample period;
  d. processing said signal so as to obtain voice characteristics of said speaker, wherein said processing includes determining a Function A, said Function A being defined as the average or maximum sound volume as a function of sound frequency, from within a range of frequencies measured in said sampled period, and wherein said processing further includes determining a Function B, said Function B defined as the averaging, or maximizing of said function A over said range of frequencies and dyadic multiples thereof;

e. comparing said voice characteristics to said reference tones so as to indicate at least one of said reference emotional status.

9. The method according to claim 1, wherein said statistical function is selected from a group comprising of; average of said function arguments; average of said function arguments, including numbers, text, and logical values; beta cumulative distribution function; the inverse of the cumulative distribution function for a specified beta distribution; individual term binomial distribution probability; one-tailed probability of the chi-squared distribution; inverse of the one-tailed probability of the chi-squared distribution; test for independence; confidence interval for a population mean; covariance, the average of the products of paired deviations; smallest value for which the cumulative binomial distribution is less than or equal to a criterion value; sum of squares of deviations; exponential distribution; probability distribution; inverse of the F probability distribution; Fisher transformation; inverse of the Fisher transformation; value along a linear trend; frequency distribution as a vertical array; result of an F-test; gamma distribution; inverse of the gamma cumulative distribution; natural logarithm of the gamma function, F(x); geometric mean; values along an exponential trend; harmonic mean; hypergeometric distribution; intercept of the linear regression line; kurtosis of a data set; k-th largest value in a data set; parameters of a linear trend; parameters of an exponential trend; inverse of the lognormal distribution; cumulative lognormal distribution; maximum value in a list of arguments; maximum value in a list of arguments, including numbers, text, and logical values; median of the given numbers; minimum value in a list of arguments; smallest value in a list of arguments, including numbers, text, and logical values; most common value in a data set; negative binomial distribution; normal cumulative distribution; inverse of the normal cumulative distribution; standard normal cumulative distribution; inverse of the standard normal cumulative distribution; Pearson product moment correlation coefficient; k-th percentile of values in a range; percentage rank of a value in a data set; number of permutations for a given number of objects; Poisson distribution; probability that values in a range are between two lim; quartile of a data set; rank of a number in a list of numbers; square of the Pearson product moment correlation coefficient; skewness of a distribution; slope of the linear regression line; k-th smallest value in a data set.

10. A computer-implemented system for apprising members of a second society about an emotional status pertaining to an emotional outbreak in a first society, said emotional status determined by sampling of M members of said first society speaking in telephone conversations, said system comprising:

a. a central computer with a processor and a non-transitory computer-readable medium (CRM) storing instructions to said processor;

b. M telephones comprising M microphones in communicative connection said with central computer; said instructions are configured for said central computer to receive and store in said CRM M simultaneous voice recordings of M people of a first society each speaking into a said microphone;

c. a display device in communicative connection with said central computer; said instructions further configured for indicating said predetermined grades of said emotional status on said display device;

said instructions are further configured for the processor to:

(i) calculate spectral functions of each said M voice recordings, comprising (i) a normalized intensity function and (ii) a maximum intensity function, and store said spectral functions in said CRM;

(ii) for each of said M voice recordings, calculate grades 1-7 according to said spectral functions and store said grades 1-7 in said CRM;

(iii) for each of said M voice recordings, add said grades 1-7 and store the grade sum in said CRM;

(iv) calculate a group grade of said emotional status of said group by applying a statistical function on said M grade sums;

(v) assign an emotional status to said first society, according to said group grade; and (vi) display a group emotional status on displays of computing devices of one or more members of a second society; said computing devices in communicative connection with said central computer;

wherein said grades 1-7, are calculated according to the following steps:

d. for calculating said grade 1:
  (i) selecting four tones in said normalized intensity function, comprising: 1) a tone with a highest intensity; 2) a tone with a second highest intensity; 3) a tone with a largest number of peaks; and 4) a tone with a second largest number of peaks;
  (ii) assigning said grade 1 according to said four tones as follows:
    1. At least two tones of: DO DO# RE REM and one or two of: SI FA FA# SOL# LA corresponding to 20;
    2. At least two tones of: SI FA FA# SOL# LA; and one or more of: DO DO# RE RE# corresponding to 20;
    3. One tone of: DO DO# RE RE#; and one or more of: SI FA FA# SOL# LA corresponding to 15;
    4. Two tones of: DO DO# RE RE#; and none of: SI FA FA# SOL# LA corresponding to 10;
    5. Two tones of: SI FA FA# SOL# LA; and none of: DO DO# RE RE# corresponding to 10;
    6. One tone of: DO DO# RE RE#; and none of: SI FA FA# SOL# LA corresponding to 5; and
    7. One tone of: SI FA FA# SOL# LA; and none of: DO DO# RE RE# corresponding to 5;

e. for calculating at least one said grade 2,
  (i) determining an S-level in said voice recordings; and
  (ii) assigning at least one said grade 2 according to said S-level as follows:
    1. change by 4 corresponds to 5;
    2. S≥20 corresponds to 20;
    3. 19≥S≥17 corresponds to 15;
       16≥S≥15 corresponds to 10;
    4. 14≥S≥13 corresponds to 5;

f. for calculating said grade 3, applicable if energy mark ≥850 Hz,
  (i) determining values, for the tones DO, DO#, RE, RE#, FA, FA#, SOL, SOL#, LA, LA#, and SI, in the normalized maximum function of an octave 4185 Hz-2092 Hz; and
  (ii) assigning said grade 3 according to said values in the normalized maximum function as follows:
    1. All higher than 60% corresponds to 20;
    2. All higher than 40% corresponds to 15;

3. All higher than 25% corresponds to 10;
4. All higher than 15% corresponds to 5;
g. for calculating said grade 4, applicable if said energy mark ≤850 Hz,
   (i) determining values, for the tones—[DO, DO#, RE, RE#, FA, FA#, SOL, SOL#, LA, LA#, SI] in the normalized maximum function of the OCTAVE 4185 Hz-2092 Hz;
   (ii) assigning said grade 4 according to said values in the normalized maximum function as follows:
      1. All higher than 60% corresponds to 10;
      2. All higher than 40% corresponds to 7.5;
      3. All higher than 25% corresponds to 5;
      4. All higher than 15% corresponds to 2.5;
h. for calculating said grade 5,
   (iii) determining a ratio in said average intensity function between 1) an intensity of each frequency in the octave (261 Hz-522 Hz); and 2) an intensity of same frequency in each of the octaves (532 Hz-1045 Hz), (1046 Hz-2092 Hz), (2092 Hz-4185 Hz); and
   (iv) assigning said grade 5 according to said ratio in said average intensity function as follows:
      1. If 1≤ratio≤1.2, to 5;
      2. If 1.21≤ratio≤1.5 10, to 10;
      3. If 1.51≤ratio≤3, to 15; and
      4. If 3≤ratio, to 20;
i. for calculating grade 6,
   (i) determining a ratio in the maximum intensity function between (i) intensity of each frequency in the octave (261 Hz-522 Hz); and (ii) intensity of same frequency in each of the octaves (532 Hz-1045 Hz), (1046 Hz-2092 Hz), (2092 Hz-4185 Hz);
   (ii) assigning said grade 6 according to said ratio in said maximum intensity function as follows:
      1. if 1≤ratio≤1.2, to 5;
      2. if 1.21≤ratio≤1.5 10, to 10;
      3. if 1.51≤ratio≤3, to 15; and
      4. if 3≤ratio, to 20; and
j. for calculating said grade 7,
   (i) determining an H-level in said voice recording; and
   (ii) assigning said grade 7 a value of 5 if there is a change in 5 points of said H-level; and
   further wherein
k. said emotional status is assigned to said group grade as follows:
   1. average grade sum ranging between 20 and 30 corresponds to an emotional status of caution;
   2. between 31 and 45 to an emotional status of mild outbreak;
   3. between 45 and 60 to outbreak;
   4. between 60 and 80 to significant outbreak; and
   5. greater than 80 to severe outbreak.

11. The system according to claim 10, wherein said high energy refers to an energy mark higher or equal to 650 HZ.

12. The system according to claim 10, wherein said high energy refers to an energy mark higher or equal to 850 HZ.

13. The system according to claim 10, wherein said determining emotional status is further performed by a matching algorithm between (i) tones of said audio data and (ii) tones of an optimal model.

14. The system according to claim 10, wherein said audio data is received from a source selected from a group consisting of: phone conversation, microphone, call application on a mobile device, microphone installed in a public location and a combination thereof.

15. The system according to claim 10, additionally comprising storage means for storing historical data.

16. The system according to claim 10, wherein said instructions are additionally for predicting future emotional state of said group by analyzing history of past emotional state.

17. The system according to claim 10, wherein said statistical function is selected from a group comprising of; average of said function arguments; average of said function arguments, including numbers, text, and logical values; beta cumulative distribution function; the inverse of the cumulative distribution function for a specified beta distribution; individual term binomial distribution probability; one-tailed probability of the chi-squared distribution; inverse of the one-tailed probability of the chi-squared distribution; test for independence; confidence interval for a population mean; covariance, the average of the products of paired deviations; smallest value for which the cumulative binomial distribution is less than or equal to a criterion value; sum of squares of deviations; exponential distribution; probability distribution; inverse of the F probability distribution; Fisher transformation; inverse of the Fisher transformation; value along a linear trend; frequency distribution as a vertical array; result of an F-test; gamma distribution; inverse of the gamma cumulative distribution; natural logarithm of the gamma function, F(x); geometric mean; values along an exponential trend; harmonic mean; hypergeometric distribution; intercept of the linear regression line; kurtosis of a data set; k-th largest value in a data set; parameters of a linear trend; parameters of an exponential trend; inverse of the lognormal distribution; cumulative lognormal distribution; maximum value in a list of arguments; maximum value in a list of arguments, including numbers, text, and logical values; median of the given numbers; minimum value in a list of arguments; smallest value in a list of arguments, including numbers, text, and logical values; most common value in a data set; negative binomial distribution; normal cumulative distribution; inverse of the normal cumulative distribution; standard normal cumulative distribution; inverse of the standard normal cumulative distribution; Pearson product moment correlation coefficient; k-th percentile of values in a range; percentage rank of a value in a data set; number of permutations for a given number of objects; Poisson distribution; probability that values in a range are between two lira; quartile of a data set; rank of a number in a list of numbers; square of the Pearson product moment correlation coefficient; skewness of a distribution; slope of the linear regression line; k-th smallest value in a data set.

18. A method for grading a match between dominant tones T1-T4 of a speaker and a given optimal model Q1-Q4 of tones, said method comprising steps of
a. receiving, by a central computer, a voice recording of a speaker speaking into a microphone in communicative connection with said central computer and storing said voice recording in a non-transitory computer readable medium (CRM) of said central computer;
b. calculating, by a processor of said central computer, a spectral function of said voice recording, said spectral function selected from a group comprising (i) a normalized intensity function and (ii) a maximum intensity function, and storing said spectral function in said CRM;
c. selecting four dominant tones in said spectral function, comprising
   1) a tone T1 with a highest intensity;
   2) a tone T2 with a largest number of peaks;
   3) a tone T3 with a second highest intensity; and
   4) a tone T4 with a second largest number of peaks;

d. finding F1, where F1 is a greatest score in Table 9 among said dominant tones T1-T4 matched to tone Q1 in said optimal model;
e. finding F2, where F2 is a greatest score in Table 9 among three remaining said dominant tones T1-T4 matched to tone Q2 in said optimal model;
f. finding F3, where F3 is a greater score in Table 9 among two remaining said dominant tones T1-T4 matched to tone Q3 in said optimal model;
g. finding F4, where F4 is a score in Table 9 of a remaining said dominant tone T1-T4 matched to tone Q4 in said optimal model; and
h. calculating a matching grade for said dominant tones to said optimal model, said matching grade given by 0.4F1+0.3F2+0.2F1+0.1F4 and storing said matching grade in said CRM.

19. The method of claim 18, further comprising steps of
a. calculating said matching grades between said dominant tones and each of the following optimal models 1-5 for Q1-Q4:
1) model 1: SOL, FA, RE, DO;
2) model 2: MI, SOL, DO, FA;
3) model 3: SOL#, FA#, RE, LAM
4) model 4: RE#, SI, DO, SOL#, measured in high energy; and
5) model 5: RE#, FA#, RE, LA; and
b. evaluating a relationship according to which said model 1-5 has a greatest said matching grade:
1) model 1: friendly showing interest talk;
2) model 2: cautious conversation;
3) model 3: warm conversation;
4) model 4: confrontational talk; and
5) model 5: desire talk;
c. displaying said relationship evaluation on a display device.

20. A system for grading a match between dominant tones T1-T4 of a speaker and a given optimal model Q1-Q4 of tones, comprising
a. a computer with a processor and a non-transitory computer-readable medium (CRM) storing instructions to said processor; and
b. a microphone in communicative connection with said computer; said instructions configured for central computer to receive and store in said CRM a voice recording of a user speaking into said microphone;
wherein said instructions are further configured for said processor to
(i) calculate a spectral function of said voice recording, said spectral function selected from a group comprising (i) a normalized intensity function and (ii) a maximum intensity function, and store said spectral function in said CRM;
(ii) select four dominant tones in said spectral function, comprising
1) a tone T1 with a highest intensity;
2) a tone T2 with a largest number of peaks;
3) a tone T3 with a second highest intensity; and
4) a tone T4 with a second largest number of peaks;
(iii) find F1, where F1 is a greatest score in Table 9 among said dominant tones T1-T4 matched to tone Q1 in said optimal model;
(iv) find F2, where F2 is a greatest score in Table 9 among three remaining said dominant tones T1-T4 matched to tone Q2 in said optimal model;
(v) find F3, where F3 is a greater score in Table 9 among two remaining said dominant tones T1-T4 matched to tone Q3 in said optimal model;
(vi) find F4, where F4 is a score in Table 9 of a remaining said dominant tone T1-T4 matched to tone Q4 in said optimal model; and
(vii) calculate a matching grade for said dominant tones to said optimal model, said matching grade given by 0.4F1+0.3F2+0.2F1+0.1F4 and store said matching grade in said CRM.

21. The system of claim 20, further comprising a display device in communicative connection with said computer, wherein said instructions are further configured to
a. calculate said matching grades between said dominant tones and each of the following optimal models 1-5 for Q1-Q4:
i. model 1: SOL, FA, RE, DO;
ii. model 2: MI, SOL, DO, FA;
iii. model 3: SOL#, FA#, RE, LAM
iv. model 4: RE#, SI, DO, SOL#, measured in high energy; and
v. model 5: RE#, FA#, RE, LA; and
b. evaluate a relationship according to which said model 1-5 has a greatest said matching grade:
i. model 1: friendly showing interest talk;
ii. model 2: cautious conversation;
iii. model 3: warm conversation; and
iv. model 4: confrontational talk; and
v. model 5: desire talk;
c. display said relationship evaluation on said display device.

* * * * *